United States Patent
Christoph et al.

(10) Patent No.: US 6,841,575 B2
(45) Date of Patent: Jan. 11, 2005

(54) USE OF 1-PHENYL-3-DIMETHYLAMINOPROPANE COMPOUNDS FOR TREATMENT OF URINARY INCONTINENCE

(75) Inventors: Thomas Christoph, Aachen (DE); Elmar Friderichs, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/448,454

(22) Filed: May 30, 2003

(65) Prior Publication Data

US 2004/0034105 A1 Feb. 19, 2004

Related U.S. Application Data

(63) Continuation of application No. PCT/EP01/13918, filed on Nov. 28, 2001.

(30) Foreign Application Priority Data

Nov. 30, 2000 (DE) .......................................... 100 59 412

(51) Int. Cl.[7] .............................................. A61K 31/135
(52) U.S. Cl. ....................................... 514/649; 514/653
(58) Field of Search ................................ 514/649, 653

(56) References Cited

U.S. PATENT DOCUMENTS

| | | | |
|---|---|---|---|
| 5,744,474 A | | 4/1998 | Thor |
| 6,248,737 B1 | * | 6/2001 | Buschmann et al. ...... 514/231.8 |
| 6,344,558 B1 | * | 2/2002 | Buschmann et al. .......... 544/86 |

FOREIGN PATENT DOCUMENTS

| | | |
|---|---|---|
| DE | 4426245 A1 | 2/1996 |
| DE | 19933421 A1 | 1/2001 |
| EP | 0176049 B1 | 9/1985 |
| EP | 0693475 A1 | 1/1996 |
| EP | 0728479 A1 | 2/1996 |
| EP | 1005861 A1 | 6/2003 |

OTHER PUBLICATIONS

C. Philippo, et al., "Asymmetric synthesis of both enantiomers of 2-(dimethylamino)-1-[3-methoxy-2(1-methylethoxy)phenyl]ethanol," Eur. J. Med. Chem. (1997) vol. 32, 881–888.

T. Yamamoto, et al., "Effects of Vamicamide on Urinary Bladder Functions in Conscious Dog and Rat Models of Urinary Frequency,"The Journal of Urology (Dec. 1995), vol. 154, 2174–2178.

A. Wein, "Pharmacologic Options for the Overactive Bladder,"Urology 51 (Supplement 2A), (Feb. 1998) 43–47.

Copy of PCT International Search Report dated Aug. 5, 2002 (receipt stamp)(PCT/EP01/13918).

Copy of German Search Report dated Aug. 4, 2003 (receopt stamp)(DE 10059412, 3).

* cited by examiner

Primary Examiner—Raymond J. Henley, III
(74) Attorney, Agent, or Firm—Crowell & Moring LLP

(57) ABSTRACT

The invention relates to the use of 1-phenyl-3-dimethylaminopropane compounds for treating increased urinary urgency or urinary incontinence, as well as to the production of corresponding medicaments.

37 Claims, No Drawings

USE OF 1-PHENYL-3-DIMETHYLAMINOPROPANE COMPOUNDS FOR TREATMENT OF URINARY INCONTINENCE

CROSS REFERENCE TO RELATED APPLICATIONS

This application is a continuation of International Patent Application No. PCT/EP01/13918, filed Nov. 28, 2001, designating the United States of America, and published in German as WO 02/43715, the entire disclosure of which is incorporated herein by reference. Priority is claimed based on Federal Republic of Germany patent application no. DE 100 59 412.3, filed Nov. 30, 2000.

FIELD OF THE INVENTION

The present invention relates to the use of 1-phenyl-3-dimethylaminopropane compounds as free bases and/or in the form of physiologically compatible salts for the production of a medicament for treating increased urinary urgency or urinary incontinence, as well as corresponding medicaments and methods for treating increased urinary urgency or urinary incontinence.

BACKGROUND OF THE INVENTION

Urinary incontinence is the involuntary passing of urine. This occurs in an uncontrolled manner if the pressure within the bladder exceeds the pressure required to close the urethra. Causes may include on the one hand an increased internal bladder pressure (e.g. due to detrusor instability) resulting in urgency incontinence, and on the other hand a reduced sphincter pressure (e.g. after childbirth or surgical intervention) resulting in stress incontinence. The detrusor is the collection of coarse bundles forming the multilayered muscular wall of the bladder, whose contraction leads to the voiding of urine, and the sphincter is the constrictor muscle of the urethra. Mixed forms of these types of incontinence as well as so-called overflow incontinence (e.g. in the case of benign prostatic hyperplasia) or reflex incontinence (e.g. following damage to the spinal cord) occur. Further details may be found in Chutka, D. S. and Takahashi, P. Y., 1998, Drugs 560: 587–595.

Urinary urgency is the state of increased bladder muscle tone ending in voiding of urine (micturition) when the bladder is almost full (or when its capacity is exceeded). This muscle tone acts as a stimulus to pass urine. Increased urinary urgency is understood in this connection to mean in particular the occurrence of premature or more frequent and sometimes even painful urinary urgency up to so-called disurea. This consequently leads to a significantly increased frequency of micturition. The causes may include, inter alia, inflammation of the bladder and neurogenic bladder disorders, as well as also bladder tuberculosis. However, all causes have not yet been elucidated.

Increased urinary urgency and also urinary incontinence are regarded as extremely unpleasant and there is therefore a clear need to achieve the greatest possible long-term improvement in patients affected by these medical conditions.

Increased urinary urgency and in particular urinary incontinence are normally treated with substances that act on the reflexes of the lower urinary tract (Wein, A. J., 1998, Urology 51 (Suppl. 21): 43–47). In general these are medicaments that have an inhibiting effect on the detrusor muscle, which is responsible for the internal bladder pressure. These medicaments include for example parasympatholytics such as oxybutynin, propiverine or tolterodine, tricyclic antidepressants such as imipramine, or muscle relaxants such as flavoxate. Other medicaments that in particular increase the resistance of the urethra or cervix of the bladder have affinities to α-adrenoreceptors such as ephedrine, to β-adrenoreceptors such as clenbutarol, or are hormones such as oestradiol. Also, certain opioids, diarylmethylpiperazines and diarylmethylpiperidines have been described for this medical condition in WO 93/15062.

In the medical conditions that are of interest here, it should be noted that in general these involve the long-term use of medicaments and, in contrast to many situations in which analgesics are used, patients are subjected to very unpleasant but not intolerable discomfort. Accordingly in this case—even more than with analgesics—care should be taken to avoid side effects if the patient does not wish to exchange one affliction for another. Furthermore, in the long-term treatment of urinary incontinence analgesic effects are also largely undesirable.

The object of the present invention was accordingly to find substances that are helpful in the treatment of increased urinary urgency or urinary incontinence and that at effective doses preferably at the same time exhibit fewer side effects and/or analgesic effects than are known from the prior art.

SUMMARY OF INVENTION

It has now surprisingly been found that compounds according to the general formula I have an outstanding effect on bladder function and accordingly are suitable for treating corresponding medical conditions.

Accordingly, the present invention provides for the use of a 1-phenyl-3-dimethylaminopropane compound according to the general formula I

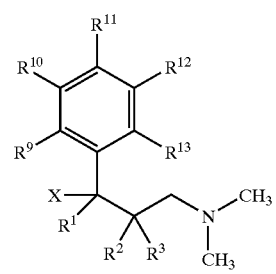

wherein

X is selected from OH, F, Cl, H or $OC(O)R^7$ where $R^7$ is selected from $C_{1-3}$-alkyl that is branched or unbranched, saturated or unsaturated, unsubstituted or singly or multiply substituted, $R^1$ is selected from $C_{1-4}$-alkyl that is branched or unbranched, saturated or unsaturated, unsubstituted or singly or multiply substituted, $R^2$ and $R^3$ are in each case selected independently of one another from H or $C_{1-4}$-alkyl that is branched or unbranched, saturated or unsaturated, unsubstituted or singly or multiply substituted, or $R^2$ and $R^3$ together form a saturated $C_{4-7}$-cycloalkyl radical that is unsubstituted or singly or multiply substituted, $R^9$ to $R^{13}$ are in each case selected independently of one another from H, F, Cl, Br, I, $CH_2F$, $CHF_2$, $CF_3$, OH, SH, $OR^{14}$, $OCF_3$, $SR^{14}$, $NR^{17}R^{18}$, $SOCH_3$, $SOCF_3$;

$SO_2CH_3$, $SO_2CF_3$, CN, $COOR^{14}$, $NO_2$, $CONR^{17}R^{18}$; $C_{1-6}$-alkyl that is branched or unbranched, saturated or unsaturated, unsubstituted or singly or multiply substituted; phenyl that is unsubstituted or singly or multiply substituted;

where $R^{14}$ is selected from $C_{1-6}$-alkyl; pyridyl, thienyl, thiazolyl, phenyl, benzyl or phenethyl, in each case unsubstituted or singly or multiply substituted; $PO(O-C_{1-4}\text{-alkyl})_2$, $CO(OC_{1-5}\text{-alkyl})$, $CONH-C_6H_4-(C_{1-3}\text{-alkyl})$, $CO(C_{1-5}\text{-alkyl})$, $CO-CHR^{17}-NHR^{18}$, $CO-C_6H_4-R^{15}$, where $R^{15}$ is ortho-$OCOC_{1-3}$-alkyl or meta- or para-$CH_2N(R^{16})_2$ where $R^{16}$ is $C_{1-4}$-alkyl or 4-morpholino, wherein in the radicals $R^{14}$, $R^{15}$ and $R^{16}$ the alkyl groups may be branched or unbranched, saturated or unsaturated, unsubstituted or singly or multiply substituted;

where $R^{17}$ and $R^{18}$ are in each case selected independently of one another from H; $C_{1-6}$-alkyl that is branched or unbranched, saturated or unsaturated, unsubstituted or singly or multiply substituted; phenyl, benzyl or phenethyl that is in each case unsubstituted or singly or multiply substituted, or $R^9$ and $R^{10}$ or $R^{10}$ and $R^{11}$ together form an $OCH_2O$, $OCH_2CH_2O$, $OCH=CH$, $CH=CHO$, $CH=C(CH_3)O$, $OC(CH_3)=CH$, $(CH_2)_4$ or $OCH=CHO$ ring, in the form of their racemates; enantiomers, diastereomers, in particular mixtures of their enantiomers or diastereomers, or an individual enantiomer or diastereomer; their bases and/or salts of physiologically compatible acids for the production of a medicament for treating increased urinary urgency or urinary incontinence.

DETAILED DESCRIPTION OF THE EMBODIMENTS

It has surprisingly been found that the aforementioned substances have a significant positive influence on certain physiological parameters that are of importance in increased urinary urgency or urinary incontinence, and thus have a positive influence either on the threshold pressure, the intercontraction interval, or on reducing the rhythmic bladder contractions and/or bladder capacity. Each one of these changes can mean a significant improvement in the symptomatic pattern of affected patients. Corresponding compounds and their production are known from DE 44 26 245 A1.

Within the context of the present invention alkyl radicals are understood to be saturated and unsaturated, branched and unbranched hydrocarbons that may also be at least singly substituted. Preferred alkyl radicals are methyl, ethyl, vinyl (ethenyl), propyl, allyl (2-propenyl), 1-propinyl, methylethyl, n-butyl, sec.-butyl, tert.-butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, $CHF_2$, $CF_3$ or $CH_2OH$.

Furthermore, cycloalkyl radicals within the context of this invention are understood to be saturated cyclic hydrocarbons that may also be at least singly substituted. Preferred cycloalkyl radicals are cyclopropyl, cyclobutyl, cyclopentyl, cyclohexyl or cycloheptyl.

In connection with alkyl and cycloalkyl, the term substituted within the context of this invention is understood to mean the substitution of an hydrogen atom by F, Cl, Br, I, $NH_2$, SH or OH, and "multiply substituted" is understood to mean that the substitution takes place on different as well as on the same atoms with the same or different substituents, for example triply on the same C atom as in the case of $CF_3$, or at different positions as in the case of —CH(OH)—CH=CH=$CHCl_2$.

In connection with phenyl, benzyl or phenethyl, the term substituted is preferably understood to mean substitution with H, F, Cl, Br, I, $CH_2F$, $CHF_2$, $CF_3$, OH, SH, $OR^{19}$, $OCF_3$, $SR^{19}$, $NH_2$, $CONH_2$, $SOCH_3$, $SOCF_3$, $SO_2CH_3$, $SO_2CF_3$, CN, $COOR^{19}$, $NO_2$; $C_{1-6}$-alkyl that is branched or unbranched, saturated or unsaturated, unsubstituted or singly or multiply substituted; phenyl that is unsubstituted;

where $R^{19}$ is selected from $C_{1-6}$-alkyl that is branched or unbranched, saturated or unsaturated, unsubstituted or singly or multiply substituted; or $C_{3-7}$-cycloalkyl.

Suitable salts within the meaning of the present invention and in each of the claimed uses are salts of the respective active ingredient with inorganic or organic acids and/or a sugar replacement such as saccharine, cyclamate or acesulfam. However, the hydrochloride is particularly preferred.

In this connection it is preferred to use compounds according to formula I in which X is selected from OH, F, Cl, $OC(O)CH_3$ or H, preferably OH, F, $OC(O)CH_3$ or H.

Furthermore, it is also preferred to use compounds according to formula I in which $R^1$ is selected from $C_{1-4}$-alkyl that is saturated and unsubstituted, branched or unbranched; preferably $CH_3$, $C_2H_5$, $C_4H_9$ or tert.-butyl, in particular $CH_3$ or $C_2H_5$.

It is also preferred to use compounds according to Formula I in which $R^2$ and $R^3$ are in each case selected independently of one another from H, $C_{1-4}$-alkyl that is saturated and unsubstituted, branched or unbranched; preferably H, $CH_3$, $C_2H_5$, i-propyl or tert.-butyl, in particular H or $CH_3$, preferably $R^3$=H, or $R^2$ and $R^3$ together form a $C_{5-6}$-cycloalkyl radical that is saturated or unsaturated, unsubstituted or singly or multiply substituted, preferably saturated and unsubstituted, in particular cyclohexyl.

It is furthermore preferred to use compounds according to formula I in which $R^9$ to $R^{13}$, wherein three or four of the radicals $R^9$ to $R^{13}$ must correspond to H, are selected independently of one another from H, Cl, F, OH, $CF_2H$, $CF_3$ or $C_{1-4}$-alkyl that is saturated and unsubstituted, branched or unbranched; $OR^{14}$ or $SR^{14}$ where $R^{14}$ is selected from $C_{1-3}$-alkyl that is saturated and unsubstituted, branched or unbranched; preferably H, Cl, F, OH, $CF_2H$, $CF_3$, $OCH_3$ or $SCH_3$ or $R^{12}$ and $R^{11}$ form a 3,4-OCH=CH ring in particular those in which, if $R^9$, $R^{11}$ and $R^{13}$ correspond to H, then one of $R^{10}$ or $R^{12}$ also corresponds to H, while the other is selected from: Cl, F, OH, $CF_2H$, $CF_3$, $OR^{14}$ or $SR^{14}$, preferably OH, $CF_2H$, $OCH_3$ or $SCH_3$, or, if $R^9$ and $R^{13}$ correspond to H and $R^{11}$ corresponds to OH, $OCH_3$, Cl or F, preferably Cl, then one of $R^{10}$ or $R^{12}$ also corresponds to H, while the other corresponds to OH, $OCH_3$, Cl or F, preferably Cl, or, if $R^9$, $R^{10}$, $R^{12}$ and $R^{13}$ correspond to H, $R^{11}$ is selected from $CF_3$, $CF_2H$, Cl or F, preferably F, or, if $R^{10}$, $R^{11}$ and $R^{12}$ correspond to H, one of $R^9$ or $R^{13}$ also corresponds to H, while the other is selected from OH, $OC_2H_5$ or $OC_3H_7$.

It is also preferred if compounds according to formula I where $R^3$=H are present in the form of the diastereomers with the relative configuration Ia

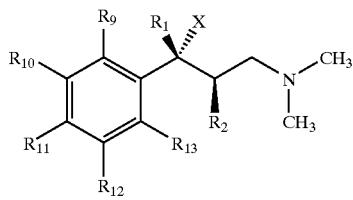

and are used in particular in mixtures with a higher proportion of this diastereomer compared to the other diastereomer or as pure diastereomer.

It is furthermore preferred if the compounds of the formula I are used in the form of the (+) enantiomer, in particular in mixtures with a higher proportion of the (+) enantiomer compared to the (−) enantiomer of a racemic compound or as pure (+) enantiomer.

In general, with the preferred use of the (+) enantiomer a smaller proportion of (−) enantiomer compared to the (+) enantiomer is also acceptable and may—but need not be—involved in the use according to the invention.

It is particularly preferred to use a compound selected from the following group:

(2RS,3RS)-1-dimethylamino-3-(3-methoxyphenyl)-2-methylpentan-3-ol, (+)-(2R,3R)-1-dimethylamino-3-(3-methoxyphenyl)-2-methylpentan-3-ol, (2RS,3RS)-3-(3,4-dichlorophenyl)-1-dimethyl-amino-2-methylpentan-3-ol, (2RS,3RS)-3-(3-difluoromethylphenyl)-1-dimethyl-amino-2-methylpentan-3-ol, (2RS,3RS)-1-dimethylamino-2-methyl-3-(3-methylsulfanylphenyl)-pentan-3-ol, (3RS)-1-dimethylamino-3-(3-methoxyphenyl)-4,4-dimethylpentan-3-ol, (2RS,3RS)-3-(3-dimethylamino-1-ethyl-1-hydroxy-2-methylpropyl)-phenol, (1RS,2RS)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (−)-(1R,2R)-3-(3-dimethylamino-1-ethyl-2-methylpropyl)-phenol, (+)-(1R,2R)-acetic acid-3-dimethylamino-1-ethyl-1-(3-methoxyphenyl)-2-methylpropyl ester, (1RS)-1-(1-dimethylaminomethylcyclohexyl)-1-(3-methoxyphenyl)-propan-1-ol, (2RS,3RS)-3-(4-chlorophenyl)-1-dimethylamino-2-methylpentan-3-ol, (+)-(2R,3R)-3-(3-dimethylamino-1-ethyl-1-hydroxy-2-methylpropyl)-phenol, (2RS,3RS)-4-dimethylamino-2-(3-methoxyphenyl)-3-methylbutan-2-ol, and (+)-(2R,3R)-4-dimethylamino-2-(3-methoxyphenyl)-3-methylbutan-2-ol, preferably as hydrochloride.

Also, if the uses according to the invention produce only slight side effects, it may for example also be advantageous in order to avoid certain types of dependence to use, in addition to compounds according to the general formula I, also morphine antagonists, in particular naloxone, naltrexone and/or levallorphan.

The invention also comprises medicaments for treating increased urinary urgency or urinary incontinence, which contain as active ingredient at least one 1-phenyl-3-dimethylaminopropane compound according to the general formula I

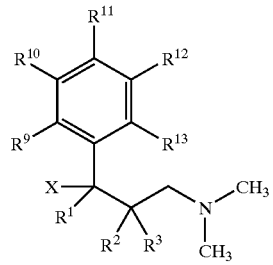

wherein

X is selected from OH, F, Cl, H or OC(O)R$^7$ where R$^7$ is selected from C$_{1-3}$-alkyl that is branched or unbranched, saturated or unsaturated, unsubstituted or singly or multiply substituted, R$^1$ is selected from C$_{1-4}$-alkyl that is branched or unbranched, saturated or unsaturated, unsubstituted or singly or multiply substituted, R$^2$ and R$^3$ are in each case selected independently of one another from H or C$_{1-4}$-alkyl that is branched or unbranched, saturated or unsaturated, unsubstituted or singly or multiply substituted, or R$^2$ and R$^3$ together form a saturated C$_{4-7}$-cycloalkyl radical that is unsubstituted or singly or multiply substituted, R$^9$ to R$^{13}$ are in each case selected independently of one another from H, F, Cl, Br, I, CH$_2$F, CHF$_2$, CF$_3$, OH, SH, OR$^{14}$, OCF$_3$, SR$^{14}$, NR$^{17}$R$^{18}$, SOCH$_3$, SOCF$_3$, SO$_2$CH$_3$, SO$_2$CF$_3$, CN, COOR$^{14}$, NO$_2$, CONR$^{17}$R$^{18}$; C$_{1-6}$-alkyl that is branched or unbranched, saturated or unsaturated, unsubstituted or singly or multiply substituted; phenyl that is unsubstituted or singly or multiply substituted;

where R$^{14}$ is selected from C$_{1-6}$-alkyl; pyridyl, thienyl, thiazolyl, phenyl, benzyl or phenethyl, in each case unsubstituted or singly or multiply substituted; PO(O—C$_{1-4}$-alkyl)$_2$, CO(OC$_{1-5}$-alkyl), CONH—C$_6$H$_4$—(C$_{1-3}$-alkyl), CO(C$_{1-5}$-alkyl), CO—CHR$^{17}$—NHR$^{18}$, CO—C$_6$H$_4$—R$^{15}$, where R$^{15}$ is ortho-OCOC$_{1-3}$-alkyl or meta- or para-CH$_2$N(R$^{16}$)$_2$ where R$^{16}$ is C$_{1-4}$-alkyl or 4-morpholino, wherein in the radicals R$^{14}$, R$^{15}$ and R$^{16}$ the alkyl groups may be branched or unbranched, saturated or unsaturated, unsubstituted or singly or multiply substituted;

where R$^{17}$ and R$^{18}$ are in each case selected independently of one another from H; C$_{1-6}$-alkyl that is branched or unbranched, saturated or unsaturated, unsubstituted or singly or multiply substituted; phenyl, benzyl or phenethyl that is in each case unsubstituted or singly or multiply substituted;

R$^9$ and R$^{10}$ or R$^{10}$ and R$^{11}$ together form an OCH$_2$O, OCH$_2$CH$_2$O, OCH=CH, CH=CHO, CH=C(CH$_3$)O, OC(CH$_3$)=CH, (CH$_2$)$_4$ or OCH=CHO ring, in the form of their racemates; enantiomers, diastereomers, in particular mixtures of their enantiomers or diastereomers, or of an individual enantiomer or diastereomer; their bases and/or salts of physiologically compatible acids as well as optionally additives and/or auxiliary substances.

Suitable salts within the context of the present invention and in each of the claimed uses are salts of the respective active ingredient with inorganic or organic acids and/or a sugar substitute such as saccharine, cyclamate or acesulfam. However, the hydrochloride is particularly preferred.

Suitable additives and/or auxiliary substances within the context of the present invention are all substances known to the person skilled in the art from the prior art for obtaining the preparation of galenical formulations. The choice of these auxiliary substances as well as the amounts thereof to be used depend on whether the medicament is to be administered orally, intravenously, intraperitoneally, intradermally, intramuscularly, intranasally, buccally or topically. For oral application preparations in the form of tablets, chewable tablets, sugar-coated pills, capsules, granules, drops, juices or syrups are suitable, while for parenteral, topical and inhalative application solutions, suspensions, readily reconstitutable dry preparations as well as sprays are suitable. A further possible form of application are suppositories for rectal use. The use in a depôt form, in dissolved form, in a carrier film or a plaster, optionally with the addition of agents promoting penetration of the skin, are examples of suitable percutaneous application forms. Examples of auxiliary substances and additives for oral application forms are disintegrants, lubricants, binders, fillers, mould release agents, optionally solvents, taste enhancers, sugars, in particular excipients, diluents, colourants, antioxidants, etc. For suppositories there may be used inter alia waxes or fatty acid esters, and for parenteral application agents there may be used excipients, preservatives, suspension auxiliaries, etc. The amounts of active ingredient to be administered to the patient vary depending on the patient's weight, on the type of application and the severity of the medical condition. The compounds according to the invention may be employed in delayed release form in preparations for oral, rectal or percutaneous use. Corresponding retard formulations, in particular in the form of a "once daily" preparation that has to be taken only once a day, are particularly preferred for use in the medical conditions covered by the invention.

Also preferred are medicaments that contain at least 0.05 to 90.0% of the active ingredient, in particular low effective dosages in order to avoid side effects or analgesic effects. Normally 0.1 to 5000 mg/kg, in particular 1 to 500 mg/kg and preferably 2 to 250 mg/kg body weight of at least one compound of the formula I are administered. However, the administration of 0.01 to 5 mg/kg, preferably 0.03 to 2 mg/kg and in particular 0.05 to 1 mg/kg body weight is also preferred and customary.

Auxiliary substances may for example include the following: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatins, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, gum arabic, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soy bean oil, lecithin, sodium lactate, polyoxyethylene fatty acid esters and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potassium carbonate, calcium phosphate, dicalcium phosphate, potassium bromide, potassium iodide, talcum, kaolin, pectin, crospovidone, agar and bentonite.

The medicaments and pharmaceutical compositions according to the invention are produced with the aid of agents, equipment, methods and processes well known in the prior art for pharmaceutical formulations, such as are described for example in "Remington's Pharmaceutical Sciences", Editor A. R. Gennaro, 17$^{th}$ Edition, Mack Publishing Company, Easton, Pa. (1985), in particular in Part 8, Chapters 76 to 93.

Thus for example, for a solid formulation such as a tablet the active ingredient of the medicament, i.e. a compound of the general structure I or one of its pharmaceutically acceptable salts, may be granulated with a pharmaceutical carrier, for example conventional tablet constituents such as maize starch, lactose, sucrose, sorbitol, talcum, magnesium stearate, dicalcium phosphate or pharmaceutically acceptable gums, and pharmaceutical diluents, such as for example water, in order to form a solid composition that contains a compound according to the invention or a pharmaceutically acceptable salt thereof in homogeneous distribution. A homogeneous distribution is understood here to mean that the active ingredient is uniformly distributed over the whole composition so that the latter can be subdivided without any difficulty into equally effective unit dose forms such as tablets, pills or capsules. The solid composition is then subdivided into unit dose forms. The tablets or pills of the medicament according to the invention or of the compositions according to the invention may also be coated or compounded in another way in order to prepare a dose form with a delayed-release action. Suitable coating agents include inter alia polymeric acids and mixtures of polymeric acids with materials such as for example shellac, cetyl alcohol and/or cellulose acetate.

Also, if the medicaments according to the invention exhibit only slight side effects it may for example be advantageous in order to avoid specific forms of dependence to use in addition to the compounds according to the general formula I also morphine antagonists, in particular naloxone, naltrexone and/or levallorphan.

Preferred are medicaments in which compounds according to the general formula I are used, in which X is selected from OH, F, Cl, OC(O)CH$_3$ or H, preferably OH, F, OC(O)CH$_3$ or H.

Also preferred are medicaments in which compounds according to the general formula I are used in which R$^1$ is selected from C$_{1-4}$-alkyl that is saturated and unsubstituted, branched or unbranched; preferably CH$_3$, C$_2$H$_5$, C$_4$H$_9$ or tert.-butyl, in particular CH$_3$ or C$_2$H$_5$.

Furthermore, medicaments are preferred in which compounds according to the general formula I are used wherein R$^2$ and R$^3$ independently of one another are selected from H, C$_{1-4}$-alkyl that is saturated and unsubstituted, branched or unbranched; preferably H, CH$_3$, C$_2$H$_5$, i-propyl or tert.-butyl, in particular H or CH$_3$, preferably R$^3$=H, or R$^2$ and R$^3$ together form a C$_{5-6}$-cycloalkyl radical that is saturated or unsaturated, unsubstituted or singly or multiply substituted, preferably saturated and unsubstituted, in particular cyclohexyl.

It is furthermore preferred if in the medicaments according to the invention compounds according to the general formula I are used in which $R^9$ to $R^{13}$, wherein three or four of the radicals $R^9$ to $R^{13}$ must correspond to H, are selected independently of one another from H, Cl, F, OH, $CF_2H$, $CF_3$ or $C_{1-4}$-alkyl that is saturated and unsubstituted, branched or unbranched; $OR^{14}$ or $SR^{14}$ where $R^{14}$ is selected from $C_{1-3}$-alkyl that is saturated and unsubstituted, branched or unbranched;

preferably H, Cl, F, OH, $CF_2H$, $CF_3$, $OCH_3$ or $SCH_3$ or $R^{12}$ and $R^{11}$ form a 3,4-OCH=CH ring, in particular compounds in which, if $R^9$, $R^{11}$ and $R^{13}$ correspond to H, then one of $R^{10}$ or $R^{12}$ also corresponds to H, while the other is selected from: Cl, F, OH, $CF_2H$, $CF_3$, $OR^{14}$ or $SR^{14}$, preferably OH, $CF_2H$, $OCH_3$ or $SCH_3$, or, if $R^9$ and $R^{13}$ correspond to H and $R^{11}$ corresponds to OH, $OCH_3$, Cl or F, preferably Cl, then one of $R^{10}$ or $R^{12}$ also corresponds to H, while the other corresponds to OH, $OCH_3$, Cl or F, preferably Cl, or, if $R^9$, $R^{10}$, $R^{12}$ and $R^{13}$ correspond to H, $R^{11}$ is selected from $CF_3$, $CF_2H$, Cl or F, preferably F, or, if $R^{10}$, $R^{11}$ and $R^{12}$ correspond to H, one of $R^9$ or $R^{13}$ also corresponds to H, while the other is selected from OH, $OC_2H_5$ or $OC_3H_7$.

It is furthermore preferred if the medicaments according to the invention contain compounds according to the general formula I where $R^3$=H, that are present in the form of the diastereomers with the relative configuration Ia

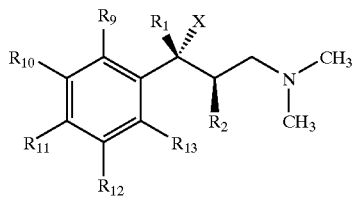

Ia in particular in mixtures with a higher proportion of this diastereomer compared to the other diastereomer, or as pure diastereomer.

It is furthermore preferred if the medicaments according to the invention contain compounds according to the general formula I that are present in the form of the (+) enantiomer, in particular in mixtures with a higher proportion of the (+) enantiomer compared to the (−) enantiomer of a racemic compound or as pure (+) enantiomer.

Generally, with the preferred use of the (+) enantiomer a smaller proportion of (−) enantiomer compared to the (+) enantiomer is also acceptable and may—but need not be—contained in the medicaments according to the invention.

Particularly preferred are medicaments according to the invention that contain at least one compound selected from the following group:

(2RS,3RS)-1-dimethylamino-3-(3-methoxyphenyl)-2-methylpentan-3-ol, (+)-(2R,3R)-1-dimethylamino-3-(3-methoxyphenyl)-2-methylpentan-3-ol, (2RS,3RS)-3-(3,4-dichlorophenyl)-1-dimethyl-amino-2-methylpentan-3-ol, (2RS,3RS)-3-(3-difluoromethylphenyl)-1-dimethyl-amino-2-methylpentan-3-ol, (2RS,3RS)-1-dimethylamino-2-methyl-3-(3-methylsulfanylphenyl)-pentan-3-ol, (3RS)-1-dimethylamino-3-(3-methoxyphenyl)-4,4-dimethylpentan-3-ol, (2RS,3RS)-3-(3-dimethylamino-1-ethyl-1-hydroxy-2-methylpropyl)-phenol, (1RS,2RS)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (−)-(1R,2R)-3-(3-dimethylamino-1-ethyl-2-methylpropyl)-phenol, (+)-(1R,2R)-acetic acid-3-dimethylamino-1-ethyl-1-(3-methoxyphenyl)-2-methylpropyl ester, (1RS)-1-(1-dimethylaminomethylcyclohexyl)-1-(3-methoxyphenyl)-propan-1-ol, (2RS,3RS)-3-(4-chlorophenyl)-1-dimethylamino-2-methylpentan-3-ol, (+)-(2R,3R)-3-(3-dimethylamino-1-ethyl-1-hydroxy-2-methylpropyl)-phenol, (2RS,3RS)-4-dimethylamino-2-(3-methoxyphenyl)-3-methylbutan-2-ol, and (+)-(2R,3R)-4-dimethylamino-2-(3-methoxyphenyl)-3-methylbutan-2-ol, preferably as hydrochloride.

The invention also provides a process for treating increased urinary urgency or urinary incontinence, in which the 1-phenyl-3-dimethylaminopropane compounds according to the invention of the general formula I are used in the form of their racemates; enantiomers, diastereomers, in particular mixtures of their enantiomers or diastereomers, or in the form of an individual enantiomer or diastereomer; as free base and/or in the form of physiologically compatible salts.

The following examples serve to illustrate the invention without however restricting the subject matter of the invention.

EXAMPLES

Example 1

List of Tested Substances

The following is a list of the compounds tested as regards their effectiveness:

| Name | Cmpd. No. |
|---|---|
| (2RS,3RS)-1-dimethylamino-3-(3-methoxyphenyl)-2-methyl-pentan-3-ol, hydrochloride | 1 |
| (+)-(2R,3R)-1-dimethylamino-3-(3-methoxyphenyl)-2-methylpentan-3-ol, hydrochloride | 2 |
| (2RS,3RS)-3-(3,4-dichlorophenyl)-1-dimethylamino-2-methylpentan-3-ol, hydrochloride | 3 |
| (2RS,3RS)-3-(3-difluoromethylphenyl)-1-dimethylamino-2-methylpentan-3-ol, hydrochloride | 4 |
| (2RS,3RS)-1-dimethylamino-2-methyl-3-(3-methylsulfanyl-phenyl)-pentan-3-ol, hydrochloride | 5 |
| (3RS)-1-dimethylamino-3-(3-methoxyphenyl)-4,4-dimethyl-pentan-3-ol, hydrochloride | 6 |
| (2RS,3RS)-3-(3-dimethylamino-1-ethyl-1-hydroxy-2-methyl-propyl)-phenol, hydrochloride | 7 |

-continued

| Name | Cmpd. No. |
|---|---|
| (1RS,2RS)-3-(3-dimethylamino-1-hydroxy-1,2-dimethyl-propyl)-phenol, hydrochloride | 8 |
| (+)-(1R,2R)-3-(3-dimethylamino-1-hydroxy-1,2-dimethyl-propyl)-phenol, hydrochloride | 9 |
| (+)-(1R,2R)-3-(3-dimethylamino-1-hydroxy-1,2-dimethyl-propyl)-phenol, hydrochloride | 10 |
| (−)-(1R,2R)-3-(3-dimethylamino-1-ethyl-2-methylpropyl)-phenol, hydrochloride | 11 |
| (+)-(1R,2R)-acetic acid-3-dimethylamino-1-ethyl-1-(3-methoxyphenyl)-2-methylpropyl ester, hydrochloride | 12 |
| (1RS)-1-(1-dimethylaminomethylcyclohexyl)-1-(3-methoxy-phenyl)-propan-1-ol, hydrochloride | 13 |
| (2RS,3RS)-3-(4-chlorophenyl)-1-dimethylamino-2-methyl-pentan-3-ol, hydrochloride | 14 |
| (−)-(2S,3S)-1-dimethylamino-3-(3-methoxyphenyl)-2-methyl-pentan-3-ol, hydrochloride | 21 |

Example 2
Cystometry Tests on Conscious Fresh Rats

Cystometry investigations were carried out on fresh female Sprague-Dawley rats according to the method of Ishizuka et. al. ((1997), Naunyn-Schmiedeberg's Arch. Pharmacol. 355: 787–793). Three days after implantation of bladder and venous catheters the animals were investigated in the conscious state while freely moving. The bladder catheter was connected to a pressure gauge and an injection pump. The animals were placed in metabolic cages that enable the volume of urine to be measured. Physiological saline solution was infused (10 ml/hour) into the emptied bladder and the bladder pressure and volume of urine were continuously recorded. After a stabilisation phase a 20-minute phase was recorded that was characterised by normal, reproducible micturition cycles. The following parameters among others were measured:

threshold pressure TP, bladder pressure immediately before micturition, bladder capacity BC, residual volume after prior micturition plus volume of infused solution during the filling phase, intercontraction interval ICI, i.e. the time interval between consecutive micturition.

An increase in the threshold pressure (TP) indicates an important therapeutic effect in one of the medical conditions covered by the invention. Also, the intercontraction interval (ICI) is an important parameter for measuring the physiological effectiveness of a substance in the treatment of urinary incontinence, as is the bladder capacity (BC). In this connection, on account of the widely differing causes of the symptoms of these disease patterns it is not necessary to influence positively all three parameters in order for a medicament to be effective. It is therefore completely sufficient if a positive effect is demonstrated in only one of these parameters in order for the medicament to be of use in urinary incontinence or increased urinary urgency.

After recording three reproducible micturition cycles to provide a baseline value, the test substances 1 (1.0 mg/kg), 2 (0.1; 0.3 and 0.5 mg/kg), 21 (0.5 mg/kg), 7 (0.3 mg/kg), 8 (1.0 mg/kg), 9 (0.5 mg/kg) and 11 (0.5 mg/kg) in a vehicle comprising 0.9% NaCl were applied intravenously and the effect on the cystometric parameters was recorded at 90 to 120 minutes. In the effect maximum the mean value of 3 micturition cycles was determined and recorded as a percentage change compared to the baseline value (Table 1).

TABLE 1

Influencing of the cystometric parameters by the test substances (change compared to the baseline value [%]); n corresponds to the number of experimental animals.

| Compound: (Concentration) | TP Threshold Pressure | BC Bladder Capacity | ICI Inter-Contraction Interval |
|---|---|---|---|
| 1 | | | |
| 1.0 mg/kg iv (n = 9) | +94%** | +31%*** | +42% |
| 2 | | | |
| 0.1 mg/kg iv (n = 5) | +28.5%** | +7.8% | +15.6% |
| 0.3 mg/kg iv (n = 8) | +122%** | +33%* | +28%* |
| 0.5 mg/kg iv (n = 9) | +77.5%** | +20.6%* | +28.6%** |
| 21 | | | |
| 0.5 mg/kg iv (n = 8) | −1.1% | +3% | +10% |
| 7 | | | |
| 0.3 mg/kg iv (n = 7) | +95%** | +32%* | +28%* |
| 8 | | | |
| 1.0 mg/kg iv (n = 8) | +60%** | +7% | +14.4% |
| 9 | | | |
| 0.5 mg/kg iv (n = 7) | +56%** | +50%** | +21%* |
| 11 | | | |
| 0.5 mg/kg iv (n = 8) | +9% | +11% | +22.6% |

The investigated substances exhibit a positive effect on the bladder regulation and are therefore suitable for treating urinary incontinence.

It was found inter alia that, of the enantiomers of the racemic compound 1, only the (+) enantiomer (compound 2) is effectively active (and thus is a particularly preferred compound of the present invention), while the (−) enantiomer (compound 21) plays only a contributory role.

Example 3
Cystometry Investigations in Narcotised Fresh Rats

The cystometric investigation was carried out on fresh female rats according to the method of Kimura et al. (Kimura et al., 1996, Int. J. Urol. 3: 218–227). The abdomen of narcotised ventilated rats is opened and the ureter is ligated. The urine is drawn off from the kidneys. A catheter is inserted into the bladder and secured in place. Saline is infused by means of an infusion pump via the catheter into the bladder until this exhibits rhythmic spontaneous activity in the form of contractions that can be recorded via a connected pressure recorder. The test substance is applied intravenously in a cumulative manner after stable starting values were reached. An effect on the bladder function is manifested by the suppression of the spontaneous contractions. The disappearance of the contractions over a period of 10 minutes serves as a parameter for their suppression.

With all the substances listed there was a measurable suppression of the spontaneous contractions in rats, Table 2 showing the mean value of the lowest dose from at least two experiments, in which contractions disappeared for the first time over a period of 10 minutes.

TABLE 2

(n corresponds to the number of the experiments involved in the value)

| Compound No. | Lowest Dose [mg/kg] |
|---|---|
| 3 | 23.3 (n = 3) |
| 4 | 1.7 (n = 3) |
| 5 | 2.3 (n = 3) |
| 6 | 16.7 (n = 3) |
| 10 | 0.2 (n = 3) |
| 12 | 30.0 (n = 3) |
| 13 | 20.0 (n = 2) |
| 14 | 20.0 (n = 2) |

The investigated substances exhibit a positive effect on bladder regulation and are thus suitable for treating urinary incontinence.

Example 4
Parenteral Application Form 1 g of the compound 2 is dissolved at room temperature in 1 l of water for injection purposes and is then adjusted to isotonic conditions by adding NaCl.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for treating increased urinary urgency or urinary incontinence in a patient in need thereof, comprising administering to said patient an effective amount of a medicament comprising a 1-phenyl-3-dimethylaminopropane compound corresponding to formula I

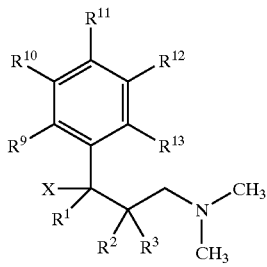

wherein
X is selected from the group consisting of OH, F, Cl, H and OC(O)$R^7$, where $R^7$ is a $C_{1-8}$-alkyl group that is branched or unbranched, saturated or unsaturated, unsubstituted or singly or multiply substituted,
$R^1$ is a $C_{1-4}$-alkyl group that is branched or unbranched, saturated or unsaturated, unsubstituted or singly or multiply substituted,
$R^2$ and $R^3$ are independently selected from the group consisting of H and $C_{1-4}$-alkyl that is branched or unbranched, saturated or unsaturated, unsubstituted or singly or multiply substituted, or $R^2$ and $R^3$ together form a $C_{4-7}$-cycloalkyl group which is saturated or unsaturated, unsubstituted or singly or multiply substituted,
$R^9$ to $R^{18}$ are independently selected from the group consisting of H, F, Cl, Br, I, $CH_2F$, $CHF_2$, $CF_3$, OH, SH, $OR^{14}$, $OCF_3$, $SR^{14}$, $NR^{17}R^{18}$, $SOOH_3$, $SOCF_3$; $SO_2CH_3$, $SO_2CF_3$, CN, $COOR^{14}$, $NO_2$, $CONR^{17}R^{18}$, —$OCH_2O$—, —$OCH_2CH_2O$—, —$OCH$=$CH$—, —$CH$=$CHO$—, —$CH$=$C(CH_3)O$—, —$OC(CH_3)$=$CH$—, —$(CH_2)_4$—, —$OCH$=$CHO$—, $C_{1-6}$-alkyl that is branched or unbranched, saturated or unsaturated, unsubstituted or singly or multiply substituted, and phenyl that is unsubstituted or singly or multiply substituted,
where $R^{14}$ is selected from the group consisting of $C_{1-6}$-alkyl, pyridyl, thienyl, thiazolyl, phenyl, benzyl, phenethyl, PO(O—$C_{1-4}$-alkyl)$_2$, CO(O$C_{1-5}$-alkyl), CONH—$C_6H_4$-($C_{1-3}$-alkyl), CO($C_{1-5}$-alkyl), CO—$CHR^{17}$—$NHR^{18}$, and CO—$C_6H_4$—$R^{15}$,
where $R^{15}$ is selected from the group consisting of ortho-OCOC$_{1-3}$-alkyl, meta-CH$_2$N($R^{16}$)$_2$, and para-CH$_2$N($R^{16}$)$_2$,
where $R^{16}$ is selected from the group consisting of $C_{1-4}$-alkyl and 4-morpholino,
where $R^{17}$ and $R^{18}$ are independently selected from the group consisting of H, phenyl, benzyl, phenethyl, and $C_{1-6}$-alkyl that is branched or unbranched, saturated or unsaturated, unsubstituted or singly or multiply substituted,
and where —$OCH_2O$—, —$OCH_2CH_2O$—, —$OCH$=$CH$—, —$CH$=$CHO$—, —$CH$=$C(CH_3)O$—, —$OC(CH_3)$=$CH$—, —$(OH_2)_4$—, and —$OCH$=$CHO$— are formed together by two adjacent radicals selected from the group $R^9$, $R^{10}$, and $R^{11}$ to produce a ring;
or a physiologically acceptable salt thereof.

2. The method of claim 1, wherein X is selected from the group consisting of OH, F, Cl, OC(O)CH$_8$, and H.

3. The method of claim 1, wherein X is selected from the group consisting of OH, F, OC(O)CH$_3$, and H.

4. The method of claim 1, wherein $R^1$ is a saturated and unsubstituted branched or unbranched $C_{1-4}$-alkyl group.

5. The method of claim 4, wherein $R^1$ is selected from the group consisting of CH$_3$, C$_2$H$_5$, n-C$_4$H$_9$, i-C$_4$H$_9$, and t-C$_4$H$_9$.

6. The method of claim 4, wherein $R^1$ is selected from the group consisting of CH$_3$ and C$_2$H$_5$.

7. The method of claim 1, wherein $R^2$ and $R^8$ are independently selected from the group consisting of H and saturated and unsubstituted, branched or unbranched $C_{1-4}$-alkyl, or $R^2$ and $R^8$ together form a $C_{5-6}$-cycloalkyl group which is saturated or unsaturated, unsubstituted or singly or multiply substituted.

8. The method of claim 7, wherein $R^2$ and $R^3$ are selected from the group consisting of H, CH$_3$, C$_2$H$_5$, i-propyl, and tert.-butyl.

9. The method of claim 7, wherein $R^2$ and $R^3$ are selected from the group consisting of H and CH$_3$.

10. The method of claim 7, wherein $R^3$ is H and $R^2$ is selected from the group consisting of H and CH$_3$.

11. The method of claim 7, wherein $R^2$ and $R^3$ together form a saturated and unsubstituted $C_{5-6}$-cycloalkyl group.

12. The method of claim 7, wherein $R^2$ and $R^3$ together form a cyclohexyl group.

13. The method of claim 1, wherein three or four of the radicals $R^9$ to $R^{13}$ are H, and the remaining radicals $R^9$ to $R^{13}$ are independently selected from the group consisting of saturated and unsubstituted, branched or unbranched $C_{1-4}$-alkyl, H, Cl, F, OH, CF$_2$H, CF$_3$, OR$^{14}$, and SR$^{14}$, or $R^{12}$ and $R^{11}$ together form a 3,4- —OCH=CH— ring, wherein $R^{14}$ is a saturated and unsubstituted, branched or unbranched $C_{1-3}$-alkyl group.

14. The method of claim 13, wherein three or four of the radicals $R^9$ to $R^{13}$ are H, and the remaining radicals $R^9$ to $R^{13}$ are independently selected from the group consisting of H, Cl, F, OH, $CF_2H$, $CF_3$, $OCH_3$ and $SCH_3$.

15. The method of claim 13, wherein $R^9$, $R^{11}$, and $R^{13}$ are H, one of $R^{10}$ and $R^{12}$ is H, and the remaining radical of $R^{10}$ and $R^{12}$ is selected from the group consisting of Cl, F, OH, $CF_2H$, $CF_3$, $OR^{14}$ and $SR^{14}$.

16. The method of claim 13, wherein $R^9$, $R^{11}$, and $R^{13}$ are H, one of $R^{10}$ and $R^{12}$ is H, and the remaining radical of $R^{10}$ and $R^{12}$ is selected from the group consisting of OH, $CF_2H$, $OCH_3$ and $SCH_3$.

17. The method of claim 13, wherein $R^9$ and $R^{13}$ are H; $R^{11}$ is selected from the group consisting of OH, $OCH_3$, Cl, and F; one of $R^{10}$ and $R^{12}$ is H; and the remaining radical of $R^{10}$ and $R^{12}$ is selected from the group consisting of OH, $OCH_3$, Cl, and F.

18. The method of claim 17, wherein $R^{11}$ is Cl.

19. The method of claim 17, wherein the remaining radical of $R^{10}$ and $R^{12}$ is Cl.

20. The method of claim 13, wherein $R^9$, $R^{10}$, $R^{12}$ and $R^{13}$ are H, and $R^{11}$ is selected from the group consisting of $CF_3$, $CF_2H$, Cl and F.

21. The method of claim 20, wherein $R^{11}$ is F.

22. The method of claim 13, wherein $R^{10}$, $R^{11}$ and $R^{12}$ are H, one of $R^9$ and $R^{13}$ is H, and the remaining radical of $R^9$ and $R^{13}$ is selected from the group consisting of OH, $OC_2H_5$ and $OC_3H_7$.

23. The method of claim 1, wherein $R^3$ is H, and wherein the compound of formula I is present in the medicament in the form of a diastereomer having the relative configuration Ia

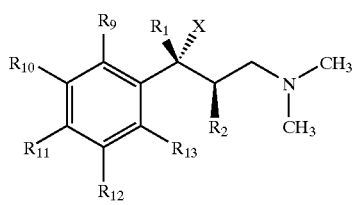

Ia

24. The method of claim 23, wherein the compound of formula I in the medicament is present as a mixture of diastereomers, wherein the proportion of the diastereomer having the configuration of formula Ia is higher than the proportion of the other diastereomer.

25. The method of claim 23, wherein the compound of formula I in the medicament is present as a pure diastereomer.

26. The method of claim 1, wherein the compound of formula I in the medicament is present in the form of the (+) enantiomer.

27. The method of claim 26, wherein the compound of formula I in the medicament is present as a mixture of enantiomers, wherein the proportion of the (+) enantiomer is higher than the proportion of the (−) enantiomer.

28. The method of claim 26, wherein the compound of formula I in the medicament is present as a pure (+) enantiomer.

29. The method of claim 1, wherein the compound of formula I is selected from the group consisting of (2RS,3RS)-1-dimethylamino-3-(3-methoxyphenyl)-2-methylpentan-3-ol, (+)-(2R,3R)-1-dimethylamino-3-(3-methoxyphenyl)-2-methylpentan-3-ol, (2RS,3RS)-3-(3,4-dichlorophenyl)-1-dimethyl-amino-2-methylpentan-3-ol, (2RS,3RS)-3-(3-difluoromethylphenyl)-1-dimethyl-amino-2-methylpentan-3-ol, (2RS,3RS)-1-dimethylamino-2-methyl-3-(3-methyl-sulfanylphenyl)-pentan-3-ol, (3RS)-1-dimethylamino-3-(3-methoxyphenyl)-4,4-dimethylpentan-3-ol, (2RS,3RS)-3-(3-dimethylamino-1-ethyl-1-hydroxy-2-methylpropyl)-phenol, (1RS,2RS)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (+)-(1R,2R)-3-(3-dimethylamino-1-hydroxy-1,2-dimethylpropyl)-phenol, (−)-(1R,2R)-3-(3-dimethylamino-1-ethyl-2-methyl-propyl)-phenol, (+)-(1R,2R)-acetic acid-3-dimethylamino-1-ethyl-1-(3-methoxyphenyl)-2-methylpropyl ester, (1RS)-1-(1-dimethylaminomethylcyclohexyl)-1-(3-methoxyphenyl)-propan-1-ol, (2RS,3RS)-3-(4-chlorophenyl)-1-dimethylamino-2-methylpentan-3-ol, (+)-(2R,3R)-3-(3-dimethylamino-1-ethyl-1-hydroxy-2-methylpropyl)-phenol, (2RS,3RS)-4-dimethylamino-2-(3-methoxyphenyl)-3-methylbutan-2-ol, and (+)-(2R,3R)-4-dimethylamino-2-(3-methoxyphenyl)-3-methylbutan-2-ol.

30. The method of claim 29, wherein the compound of formula I is present as a hydrochloride salt.

31. The method of claim 1, wherein $R^{14}$ is selected from the group consisting of $C_{1-6}$-alkyl, pyridyl, thienyl, thiazolyl, phenyl, benzyl, and phenethyl, and wherein the $R^{14}$ radical is further substituted.

32. The method of claim 1, wherein at least one of the radicals $R^{14}$, $R^{15}$, and $R^{16}$ contains a branched alkyl group.

33. The method of claim 1, wherein at least one of the radicals $R^{14}$, $R^{15}$, and $R^{16}$ contains a substituted alkyl group.

34. The method of claim 1, wherein at least one of the radicals $R^{14}$, $R^{15}$, and $R^{16}$ contains a saturated alkyl group.

35. The method of claim 1, wherein at least one of the radicals $R^{17}$ and $R^{18}$ is selected from the group consisting of phenyl, benzyl, and phenethyl, and wherein the at least one radical is substituted.

36. The method of claim 1, wherein the compound of formula I is present in the form of a base.

37. The method of claim 1, wherein the compound of formula I is present in the form of a salt of a physiologically acceptable acid.

* * * * *